US007683927B2

(12) United States Patent
Higuchi et al.

(10) Patent No.: US 7,683,927 B2
(45) Date of Patent: Mar. 23, 2010

(54) ELECTRONIC ENDOSCOPE APPARATUS

(75) Inventors: Mitsuru Higuchi, Saitama (JP); Minoru Iketani, Saitama (JP)

(73) Assignee: Fujinon Corporation, Saitama-shi (JP)

( * ) Notice: Subject to any disclaimer, the term of this patent is extended or adjusted under 35 U.S.C. 154(b) by 1567 days.

(21) Appl. No.: 10/959,184

(22) Filed: Oct. 7, 2004

(65) Prior Publication Data

US 2005/0088518 A1 Apr. 28, 2005

(30) Foreign Application Priority Data

Oct. 8, 2003 (JP) ............................ 2003-348918

(51) Int. Cl.
*A61B 1/04* (2006.01)

(52) U.S. Cl. ........................................................ 348/74

(58) Field of Classification Search ....................... None
See application file for complete search history.

(56) References Cited

U.S. PATENT DOCUMENTS 5,742,823 A * 4/1998 Edwards et al. ............. 718/102
6,184,922 B1 * 2/2001 Saito et al. .................... 348/65
6,295,082 B1 * 9/2001 Dowdy et al. ................. 348/72
6,741,534 B1 * 5/2004 Takahashi et al. ........ 369/47.14

FOREIGN PATENT DOCUMENTS

JP 2000-287203 10/2000

* cited by examiner

*Primary Examiner*—Nhon T Diep
(74) *Attorney, Agent, or Firm*—Birch, Stewart, Kolasch & Birch, LLP

(57) ABSTRACT

An electronic endoscope apparatus, comprising a media drive unit for recording image data, which is given digital processing, in a recording medium, judges a recordable amount of images by the detection of a free space of the above-mentioned recording medium, and displays a message, prompting the replacement of the recording medium in a monitor when this recordable amount becomes zero. Then, when the recording medium is replaced during the examination of the same patient, the electronic endoscope apparatus automatically creates a folder for a patient in this recording medium, and records remaining image data in this folder for a patient. In addition, also when the recordable amount becomes zero after the examination end switch was pushed, the electronic endoscope apparatus automatically creates a folder for the patient in a replaced recording medium, and records remaining image data in this folder.

6 Claims, 4 Drawing Sheets

The medium is FULL. Replace the medium.
20
12
10
14A
15
70A
FIRST PIECE
FOLDER $K_1$ FOR PATIENT
19
16A
ADDITION
70B
11
14B
16
18
17
44
AUTOMATIC CREATION OF FOLDER $K_1$ FOR PATIENT TURN-ON OF RECORD SWITCH
CAPTURE IMAGE DATA INTO IMAGE STORAGE MEMORY
201
C
202
IS A RECORDABLE AMOUNT TO THE MEDIUM ZERO?
N
Y
203
DISPLAY "Medium is FULL. Replace the medium. Yes or No (for confirmation)"
204
YES OR NO ?
N
Y
205
IS A FOLDER FOR A CURRENT PATIENT CREATED?
N
Y
206
TRANSFER PATIENT DATA TO THE MEDIUM AGAIN
207
CREATE A FOLDER FOR THE PATIENT IN THE MEDIUM
208
WRITE IMAGE DATA INTO THE FOLDER FOR THE PATIENT IN THE MEDIUM
END

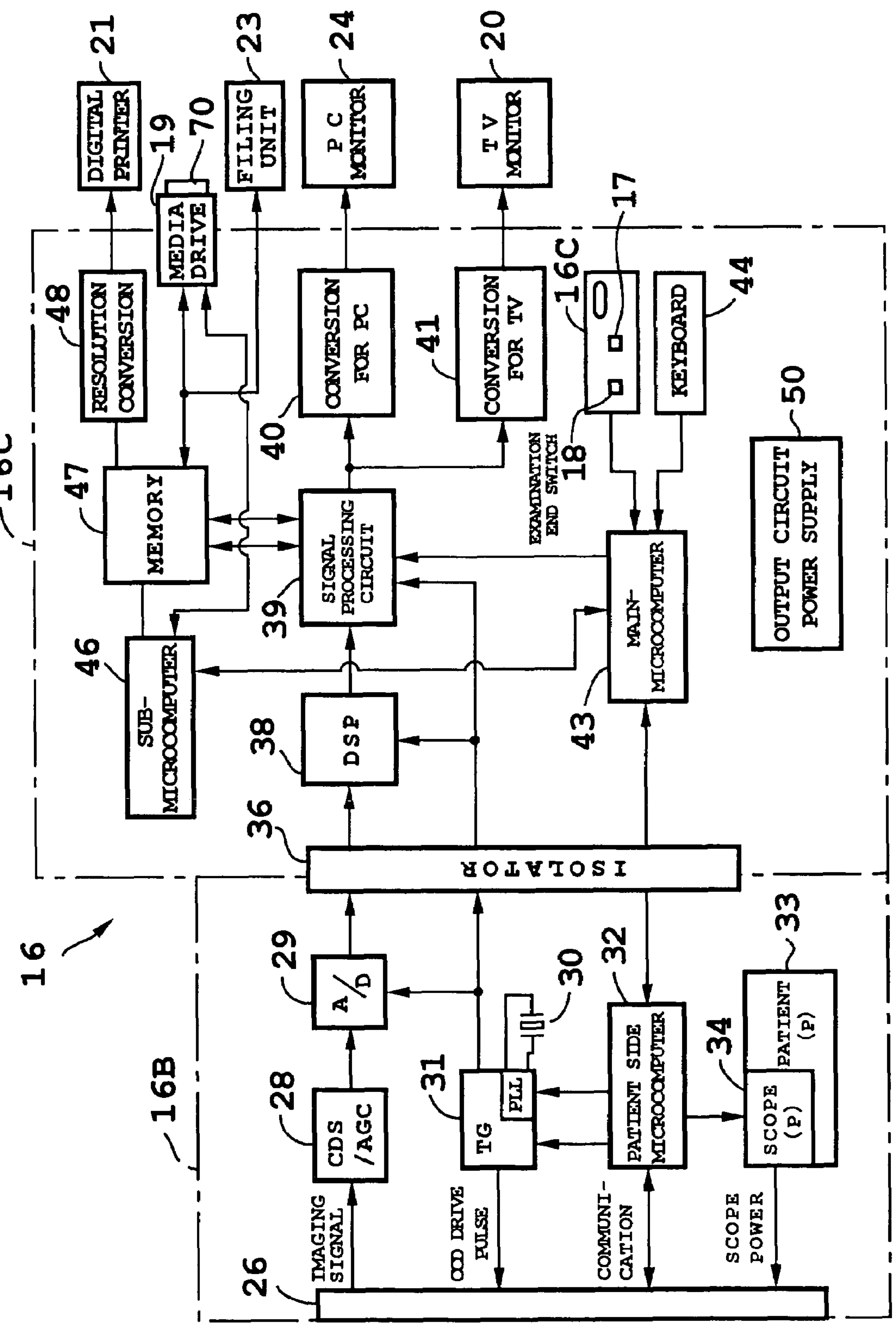
FIG.1
16
16B
16C
DIGITAL PRINTER
21
MEDIA DRIVE
19
70
FILING UNIT
23
P C MONITOR
24
T V MONITOR
20
RESOLUTION CONVERSION
48
CONVERSION FOR PC
40
CONVERSION FOR TV
41
17
18
EXAMINATION END SWITCH
KEYBOARD
44
MEMORY
47
SIGNAL PROCESSING CIRCUIT
39
MAIN-MICROCOMPUTER
43
OUTPUT CIRCUIT POWER SUPPLY
50
SUB-MICROCOMPUTER
46
DSP
38
ISOLATOR
36
A/D
29
CDS /AGC
28
TG
PLL
31
30
PATIENT SIDE MICROCOMPUTER
32
PATIENT (P)
33
SCOPE (P)
34
IMAGING SIGNAL
CCD DRIVE PULSE
COMMUNI-CATION
SCOPE POWER
26

ELECTRONIC ENDOSCOPE APPARATUS

BACKGROUND OF THE INVENTION

The application claims the priority of Japanese Patent Applications No. 2003-348918 filed on Oct. 8, 2003 which is incorporated herein by reference.

FIELD OF THE INVENTION

The present invention relates to an electronic endoscope apparatus, and in particular, to the structure of an electronic endoscope apparatus which forms a digital image of an object on the basis of an output signal of a solid state image pickup device mounted in an electronic scope and can save this image data in a recording medium.

DESCRIPTION OF THE RELATED ART

An electronic endoscope apparatus is equipped with a solid state image pickup device such as a CCD (Charge Coupled Device) in an end section of an electronic scope (electronic endoscope). This CCD images an object on the basis of the illumination of light from light equipment. It becomes possible to display an image of the object on a monitor and to record a still image etc. In a recording apparatus, by outputting an imaging signal obtained by this CCD to a processor unit, and giving various kinds of graphic processing in the processor unit.

As shown also in Japanese Patent Laid-Open No. 2000-287203, this kind of electronic endoscope apparatus performs not only analog processing for outputting an object image to a normal NTSC (PAL) system monitor, but also digital image processing to output the object image to various kinds of external digital equipment such as a personal computer monitor and to use the image.

By the way, in recent years, since CCDs which are solid state image pickup devices have been made to be in high pixel counts and high resolutions, it is proposed to form digital images where image information obtained by the CCDs with high pixel counts is employed efficiently. That is, in personal computers, for example, there are standards such as VGA (Video Graphics Array), XGA (Extended Graphics Array), and SXGA (Super XGA) whose display pixel counts are different. When forming an image signal corresponding to one of these standards, it becomes possible to use the image signal in external digital equipment. Then, as recording media for use in these external equipment, there are a PC card, Smart Media (registered trademark), a COMPACTFLASH (registered trademark), an MO, and the like, and it is performed to record and store endoscope image data in these recording media.

Nevertheless, since the data volume of the above-mentioned recording media is not so large though the size of one high-resolution image is large (data volume per image is large), there may be the case that the capacity of a recording medium becomes insufficient in the middle of endoscopy. In such a case, there is a problem that it becomes complicated to judge the replacement timing of the recording medium and to perform operations such as resetting of the patient data to a new recording medium. Namely, when an endoscope image is recorded in a recording medium, it is performed to create a folder for a patient in the recording medium on the basis of the entry of data about the patient such as a name, discrimination information (ID), and an age, and to write image data in the folder for this patient. Hence, when the recording medium is replaced, it becomes necessary to redo such an operation and processing.

The present invention is made in view of the above-described problems, and aims at providing an electronic endoscope apparatus which can easily record image data in a recording medium even when the recording medium must be replaced during an examination by an endoscope.

SUMMARY OF THE INVENTION

In order to achieve the above-described object, an electronic endoscope apparatus of the present invention is characterized in comprising a recording medium (information medium) which records the image data of an object which is formed on the basis of an output of a solid state image pickup device mounted in an electronic scope, judging means which judges a recordable amount of the above-mentioned images in the above-mentioned recording medium during an examination, a display processing circuit which displays a recording medium exchange message on a display unit when the above-mentioned recordable amount becomes zero, and a control circuit which performs control so as to automatically create a folder for a patient in this recording medium and to record remaining image data in this folder for the patient, when the above-mentioned recording medium is replaced when the record of the image data under one examination of the same patient in the above-mentioned recording medium is not completed.

In addition, another invention is characterized in comprising a recording medium which records the image data of an object which is formed on the basis of an output of a solid state image pickup device mounted in a scope, judging means which judges a recordable amount of the above-mentioned images in the above-mentioned recording medium during an examination, a display processing circuit which displays a recording medium exchange message on a display unit when the above-mentioned recordable amount becomes zero, and an examination end switch which terminates a function of the above-mentioned electronic scope (turning off only a power supply of the electronic scope and maintaining the ON state of the power supply of a processor unit which processes the image data of the object), image storage memory which saves image data in at least one examination of the same patient, and a control circuit which performs control so as to automatically create a folder for a patient in this recording medium and to record remaining image data in this folder for the patient, when the above-mentioned examination end switch is pushed and the above-mentioned recording medium is replaced while the image data is transferred to the above-mentioned recording medium from this image storage memory.

According to the above-mentioned invention, a recordable amount is judged by detecting a free space (remaining space) of a recording medium. When this recordable amount becomes zero, a message prompting the replacement of the recording medium is displayed in a display unit. Then, when the recording medium is replaced during the examination of the same patient, a folder for the patient is automatically created in this recording medium, and remaining image data is recorded in this folder for the patient.

In addition, CCDs with high pixel counts are used in recent units. Nevertheless, since the size of one image obtained with such a CCD is large (an amount of data per image is large), the transmission time of the image data becomes long. Hence, if the completion of record processing in a recording medium is waited, endoscopy cannot be conducted smoothly. In order to solve this, in the present invention, the image storage memory which saves the image data for at least one examination is provided. Nevertheless, since record processing in the recording medium is not completed in spite of endoscopy being ended, there arises a situation that the electronic scope cannot be removed from the processor unit. That is, although washing and disinfection of the electronic scope must be performed and connection of another electronic scope is necessary in preparation for the following examination after endoscopy is ended, the next operation cannot be performed smoothly when the record processing in the recording medium is not completed.

Then, in another invention, for example, an examination end switch which turns off only an electronic scope and terminates a scope function is provided. Even when the recording medium is replaced after this examination end switch is pushed, a folder for the patient is automatically created in this recording medium, and the remaining image data is contained in this folder for the patient.

According to such electronic endoscope apparatus, the recording of image data in a recording medium is easily performed, and also does not interfere with an examination. In addition, even when the recording medium is replaced after the function of an electronic scope is terminated, recording in the recording medium is similarly performed, and hence, it becomes possible to easily record all examination image data.

BRIEF DESCRIPTION OF THE DRAWINGS

FIG. 1 is a circuit block diagram showing the structure of an electronic endoscope apparatus according to an embodiment of the present invention;

DETAILED DESCRIPTION OF THE PREFERRED EMBODIMENTS

Figure 2:
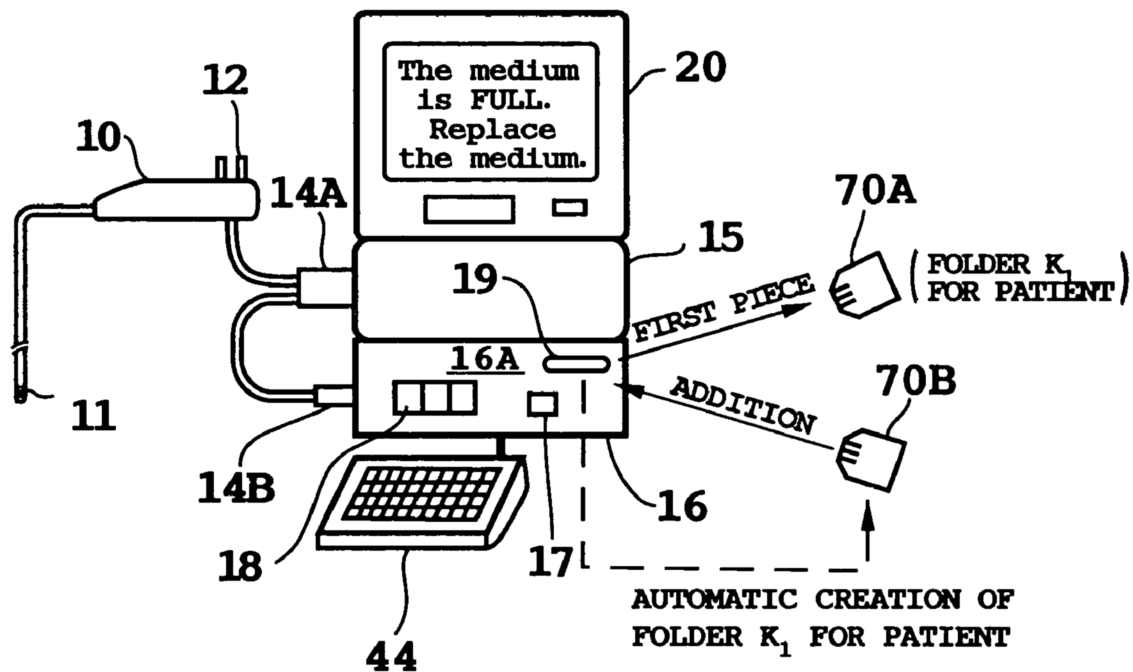
FIG. 2 is a schematic diagram showing the whole structure of the electronic endoscope apparatus according to the embodiment.

FIGS. 1 and 2 show the structure of an electronic endoscope apparatus according to an embodiment, and the whole structure will be explained first on the basis of FIG. 2. As shown in FIG. 2, a CCD 11 which is a solid state image pickup device is provided in an end section of an electronic scope (electronic endoscope) 10. As this CCD 11, CCDs with various kinds of pixel counts of 35 or 65 million pixels, for example are mounted. In an operation unit of this electronic scope 10, control switches such as a freeze/record button 12 are located. This electronic scope 10 is connected not only to light equipment 15 through a light guide connector 14A, but also to a processor unit 16 through a signal/power supply line connector 14B. The light of the above-mentioned light equipment 15 is supplied to the end section through a light guide located in the electronic scope 10. An object is imaged by the above-mentioned CCD 11 owing to illumination light emitted from this end section.

In a front operation panel 16A of the above-described processor unit 16, not only a main power supply switch (manual operation button) 17, and an examination end switch (i.e., a scope power-off switch) 18 are located, but also a loading slot of a media drive unit (drive) 19 which is located inside is provided. This media drive unit 19 writes and reads data between with a recording medium 70 such as a PC card, Smart Media, COMPACTFLASH, and an MO. In addition, an NTSC (PAL) system TV monitor 20, and a digital printer 21, a filing unit 23, and a personal computer (PC) monitor 24 which are shown in FIG. 1, and the like are connected to this processor unit 16.

FIG. 1 shows the detailed structure in the processor unit 16. This processor unit 16 has a patient circuit 16B which performs predetermined graphic processing, and an output circuit 16C which forms a signal corresponding to various kinds of output forms. The signal/power line connector 14B in the side of the above-mentioned electronic scope 10 is connected to the signal/power line connector 26. In the above-mentioned patient circuit 16B, a CDS/AGC (correlation double sampling/automatic gain control) circuit 28 which samples and amplifies a picture signal inputted from the CCD 11, an A/D converter 29, a crystal oscillator 30, a timing generator (TG) 31 which forms a CCD drive pulse, supplied to the electronic scope 10, a synchronizing signal, etc., and a patient side microcomputer 32 which communicates with the electronic scope 10 and controls the patient circuit 16B are provided.

Since the example concerned is constructed so that only the power supply of the electronic scope 10 can be switched off at the examination end switch 18 so as to terminate a function of the electronic scope 10, a patient power supply unit (P) 33 and a scope power supply unit (P) 34 which supplies power to the electronic scope 10 through the signal/power line connector 26 are provided. The switching of the power supply in this scope power supply unit 34 is controlled by the patient side microcomputer 32.

An output circuit 16C is connected to the patient circuit 16B through an isolator (electrical isolation means) 36. In this output circuit 16C, a DSP (Digital Signal Processor) 38 and a signal processing circuit 39 which give various kinds of image processing to the picture signal which is supplied from the A/D converter 29 and is digitized, a resolution conversion circuit 40 for PC which converts an output of this signal processing circuit 39 into predetermined resolution (for example, image sizes such as VGA and XGA) for displaying the output on the personal computer monitor 24, and a resolution conversion circuit 41 for TV which converts the output of this signal processing circuit 39 into an analog signal (Y/C signal etc.) in resolution (image size) for displaying the output on the NTSC (PAL) system TV monitor 20 are provided. The above-mentioned signal processing circuit 39 has a character generator etc., generates messages (characters etc.) relating to the amount of images already recorded (written) in the recording medium 70, the recordable image amount (remaining amount) in a free space, which is calculated on the basis of a pixel count of the electric scope 10 connected, a data compression rate set in the operation panel 16A or the like, and the replacement of the recording medium 70, and performs image mixing processing for displaying the characters on a monitor screen.

In addition, a main microcomputer 43 which totally controls the circuits in the processor unit 16, and performs the display control of the recordable amount in the recording medium 70 and judges a recordable amount in the recording medium 70 on the basis of information on a free space which is outputted from the sub-microcomputer 46 described later, and the time of this amount becoming zero. To this main microcomputer 43, each control signal of the switches 17, 18, and the like which are located at the operation panel 16A is supplied. Then, the sub-microcomputer 46 which controls the writing, reading, etc. of image data to the below-mentioned memory 47, controls the media drive unit 19, and detects the free space of the recording medium 70, and image storage memory 47 which can store at least one set of examination data (for example, nearly 100 images) so as to output examination images are provided.

That is, in order to receive an output of this image storage memory 47, the media drive unit 19 is connected. The above-mentioned sub-microcomputer 46 accesses the recording medium 70 inserted in this recording medium drive unit 19 to detect the free space (empty state) of this recording medium 70. In addition, so as to output the examination images to the digital printer 21 mentioned above, a resolution conversion circuit 48 which forms a digital image signal corresponding to standards such as VGA, XGA, and SXGA is provided in the above-mentioned image storage memory 47. Furthermore, an output circuit power supply unit (P) 50 is located in this output circuit 16C.

The embodiment has the above structure, and its operation will be described with referring to FIGS. 3 to 5. First, when the main power supply switch 17 of the operation panel 16A is pushed, power is supplied from the power supply units 50, 33, and 34 to each circuit, and image pickup by the CCD 11 at the end of the electronic scope 10 is started. A picture signal outputted from this CCD 11 is given various kinds of digital image processing by the CDS/AGC circuit 28, A/D converter 29, DSP 38, and signal processing circuit 39. The picture signal is supplied through the resolution conversion circuit 40 for PC to the PC monitor 24, or through the resolution conversion circuit 41 for TV to the TV monitor 20, and the object image is displayed on each monitor.

Here, when the recording medium 70 is inserted into the media drive unit 19, the sub-microcomputer 46 detects the free space in this recording medium 70 to transmit this free space signal to the main microcomputer 43. Since the data volume of one image is grasped from a pixel count of the CCD 11 mounted in the electronic scope 10, this main microcomputer 43 calculates a recordable amount from this data capacity of one image and the above-mentioned free space. Then, this recordable amount and the amount already recorded, and the like are displayed on the screen of the monitor 20.

Figure 3:
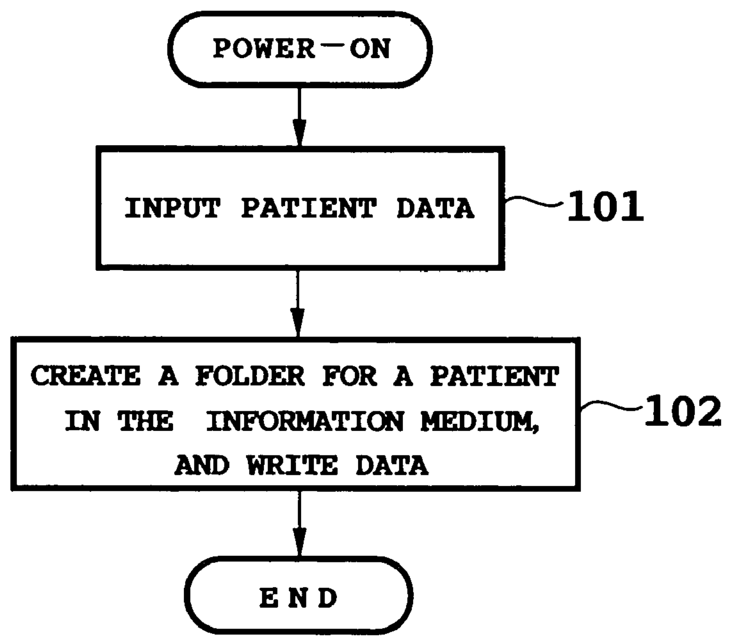
FIG. 3 is a flowchart showing the operation of relating to the creation of a folder for a patient in the embodiment.

On the other hand, as shown in FIG. 3, when data such as a name, an ID, and an age which are patient data are inputted with a keyboard 44 (step 101) after the above-mentioned main power supply switch 17 was turned on, a folder for a patient with a folder name $K_1$ which comprises, for example, the name and ID of the patient, a date, and the like is automatically created at the next step 102. Then, patient data is written into this folder $K_1$ for the patient (a first piece of recording medium 70A in FIG. 2).

Then, when the freeze switch of the freeze/record button 12 of the electronic scope 10 which is a first step is pushed, a still image contained in the image memory in each of the resolution conversion circuits 40 and 41 (frame memory etc.) is displayed on the TV monitor 20 or PC monitor 24. At the same time, this image data at the time of freeze is supplied to the image storage memory 47. Next, when a record switch of the freeze/record button 12 which is a second step is pushed with looking at the screen of the above-mentioned TV monitor 20, recording in the recording medium 70 is performed in the operation shown in FIG. 4.

Figure 4:
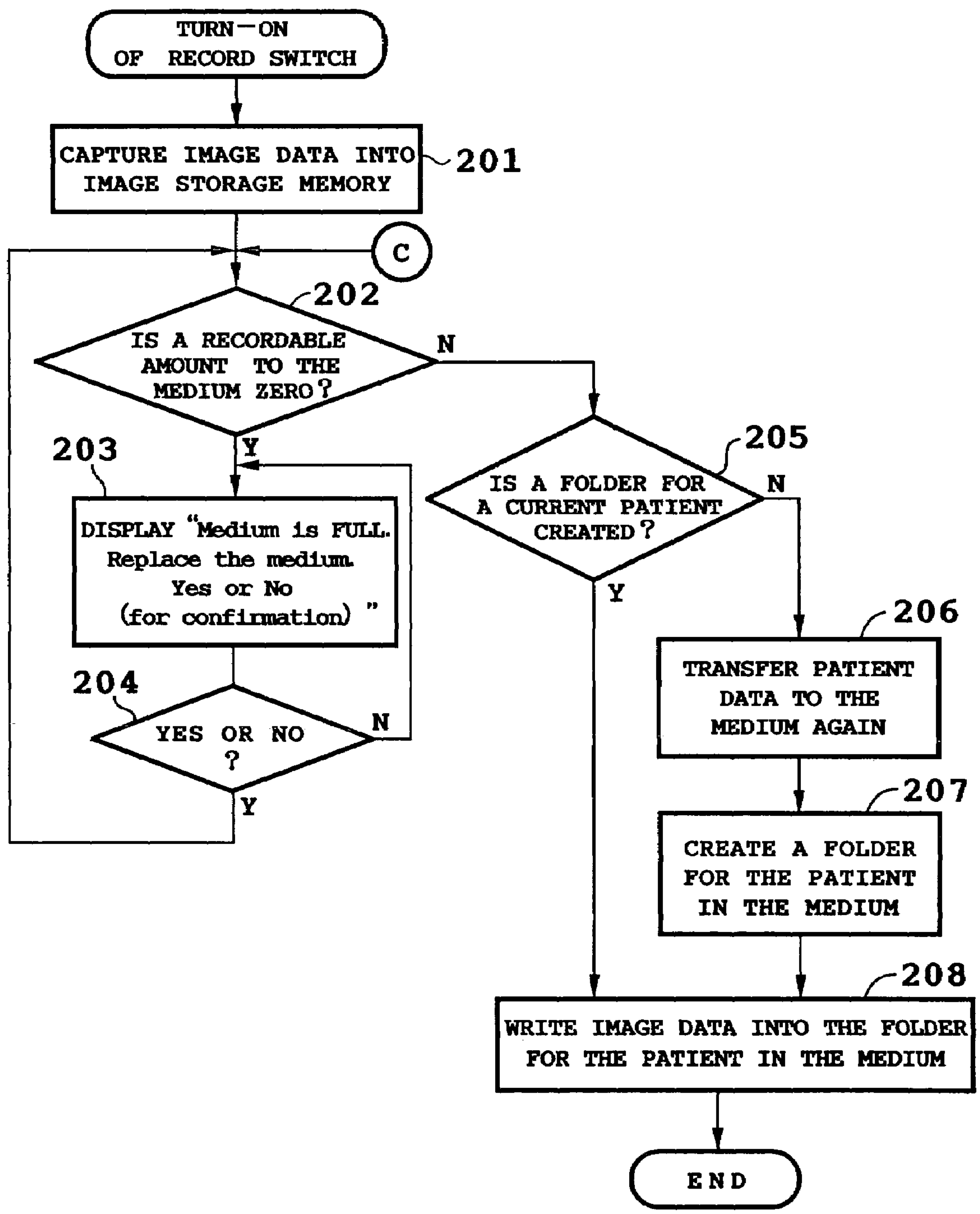
FIG. 4 is a flowchart showing the recording operation of a still image in a recording medium in the embodiment.

In FIG. 4, when the record switch is pressed, a still image currently written in the above-mentioned image storage memory 47 is maintained and saved at step 201. It is judged at the next step 202 whether the recordable amount to the recording medium 70 is zero (the medium is full). In addition, it is judged at step 205 whether the folder $K_1$ for the current patient is created. Here, since a first piece of recording medium 70A in FIG. 2 is new and has a free space, the judgment at step 202 is N (No) and the judgment at step 205 is Y (YES). Then, the media drive unit 19 writes the image data of the above-mentioned still image in this recording medium 70A under the control of the sub-microcomputer 46.

Then, when the recordable amount of this recording medium 70A becomes zero, and judgment at the above-mentioned step 202 becomes "Y" meaning that the recordable amount is zero, for example, "The medium is Full. Replace the medium. Yes or No (display of a confirmation key or selection key)" is displayed at the next step 203. That is, these are displayed on the monitor 20 by generating the above-mentioned characters with a character generator in the signal processing circuit 39 in FIG. 1 and mixing them with the current image signal. Here, when the medium is replaced to a next new recording medium 70B as shown in FIG. 2, and it is judged that Yes (Y) of the selection key is selected at step 204, the process returns to the step 202, and it is judged once again whether the recordable amount is zero. That is, when the new recording medium 70B is inserted in the media drive unit 19, the sub-microcomputer 46 calculates a recordable amount, and judges from this calculation result whether the recordable amount is zero.

Since this recording medium 70B is new, judgment at step 202 becomes N and a folder for a patient is not created, and hence, judgment at a next step 205 also becomes N. Accordingly, in this case, patient data is transferred to the recording medium 70B (step 206), a folder $K_1$ for a patient is created automatically in this recording medium 70B (step 207), and the remaining image data contained in the image storage memory 47 is written into this folder $K_1$ (step 208).

In the above-mentioned recording operation, the image storage memory 47 has the capacity of being able to store the image data for at least one examination. Hence, there arises the situation that, even after the endoscopy for a patient was ended, the recording operation to the recording medium 70 is not completed. Then, in the embodiment, only the function of the electronic scope 10 can be ended (only the power supply is turned off) by the examination end switch 18, and operation in this case is shown in FIG. 5.

Figure 5:
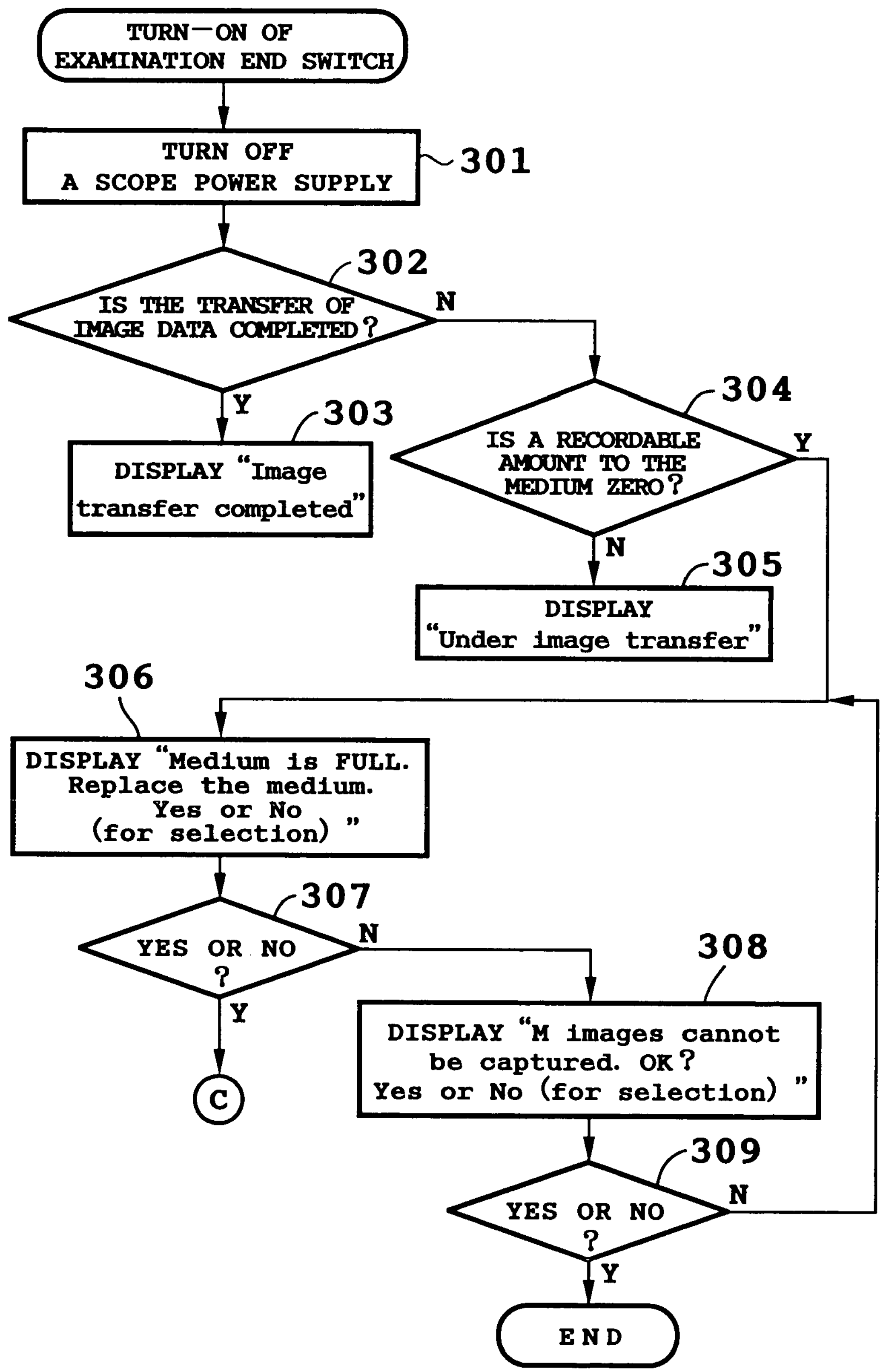
FIG. 5 is a flowchart showing the recording operation of a still image in a recording medium at the time of pushing an examination end switch in the embodiment.

In FIG. 5, when the examination end switch 18 is turn on, the scope power supply unit 34 is turned off (cutoff) at step 301. That is, the main microcomputer 43 outputs a command of scope power-off to the patient side microcomputer 32. Then, only the scope power supply unit 34 is turned off by the control of this patient side microcomputer 32. Here, when the CCD drive pulse is outputted from the timing generator 31, an output of this CCD drive pulse is first stopped (OFF), and next, when the patient side microcomputer 32 communicates with the electronic scope 10 side, the scope power supply unit 34 is turned off after stopping this communication. At this time, since the patient power supply unit 33 and output circuit power supply unit 50 are not turned off, the output (writing) of the image data to the recording medium 70A is performed continuously. Accordingly, since the electronic scope 10 can be removed from the processor unit 16 before the recording operation is completed, it becomes possible to quickly perform the next operation such as washing of the electronic scope 10, and connection of another electronic scope for the following examination.

It is judged at the next step 302 whether the transfer of image data is completed, and when the judge is Y, "Image transfer completed" is displayed on the monitor 20 (step 303). On the other hand, when being N, it is judged at the next step 304 whether the recordable amount to the recording medium 70B is zero. When being N, "Under image transfer" is displayed on the monitor 20, and when being Y, the process goes to step 306. At this step 306, "The medium is FULL. Replace the medium. Yes or No (a confirmation key)" is displayed.

When Yes of the confirmation key is selected after the medium being replaced to the additional recording medium 70B with the confirming this display, the judgment becomes Y at the next step 307, and the process goes to step 202 in FIG. 4 through a connection symbol C. Accordingly, also in this case, as mentioned above, after confirming at step 205 that the folder for the current patient is not created, the folder $K_1$ for the patient is automatically created in the recording medium 70B. The remaining image data contained in the image storage memory 47 is written into this folder $K_1$ (steps 206 to 208).

On the other hand, when the recording medium 70 is not replaced and the judgment becomes N at step 307 in the above-mentioned FIG. 5, "M (an amount left in the media 47 for image storage) images are not captured. OK? Yes or No (a confirmation key)" is displayed at step 308. Then, the recording operation is ended when the selection of Yes is judged at the next step 309.

In the above-mentioned embodiment, although the case that the media drive unit 19 is incorporated in the processor unit 16 is explained, it is possible to apply the present invention also when external media equipment having a media drive unit is connected to the processor unit 16. In addition, other recording media such as an MO disk may be used as a recording medium. Furthermore, although a recording medium replacement message and the like are displayed on the screen of the monitor 20, a liquid crystal display or the like may be also provided, for example, in the operation panel 16A as this display unit.

What is claimed is:

1. An electronic endoscope apparatus, comprising:

a recording medium which records image data of an object which is formed on the basis of an output of a solid state image pickup device mounted in an electronic scope;

judging unit which judges a recordable amount of the image in the recording medium during an examination;

a display processing circuit which displays a recording medium exchange message on a display unit when the recordable amount becomes zero; and a control circuit which performs control so as to automatically create a folder for a patient in this recording medium and record image data in this folder for the patient, and when the record of the image data under one examination of the same patient in the recording medium is not completed and the recording medium is replaced with another recording medium, while said electronic scope is functioning performs control so as to transfer patient data to said another recording medium and automatically create another folder for said patient in said another recording medium and record remaining image data in said another folder.

2. The electronic endoscope apparatus according to claim 1, wherein the display processing circuit displays a recordable amount, which is judged by the judging unit, on a display unit.

3. The electronic endoscope apparatus according to claim 1, further comprising image memory which once stores image data of an object obtained by the solid state image pickup device and has the capacity of being able to save image data in at least one examination of the same patient.

4. An electronic endoscope apparatus, comprising:

a recording medium which records image data of an object which is formed on the basis of an output of a solid state image pickup device mounted in an electronic scope;

judging unit which judges a recordable amount of the image in the recording medium during an examination;

a display processing circuit which displays a recording medium exchange message on a display unit when the recordable amount becomes zero;

an examination end switch which terminates a function of the electronic scope;

image storage memory which saves image data in at least one examination of the same patient; and a control circuit which performs control so as to automatically create a folder for a patient in this recording medium and record image data in this folder for the patient, and when the transferring of the image data to the recording medium from the image storage memory is not completed and the examination end switch is pushed to terminate the activity of the electronic endoscope and when the recording medium is replaced with another recording medium, performs control so as to transfer patient data to said another recording medium and automatically create another folder for said patient in said another recording medium and record remaining image data in said another folder.

5. The electronic endoscope apparatus according to claim 4, wherein the display processing circuit displays a recordable amount, which is judged by the judging unit, on a display unit.

6. The electronic endoscope apparatus according to claim 4, wherein the examination end switch turns off only a power supply of the electronic scope, and a power supply of a processor unit which processes image data of an object maintains an ON state.

* * * * *